United States Patent [19]

Baumgarth et al.

[11] Patent Number: 5,036,068
[45] Date of Patent: Jul. 30, 1991

[54] 4-(PYRIDYL)- AND 4-(OXO-PYRIDYL)-1,3-BENZOXAZINES

[75] Inventors: Manfred Baumgarth, Darmstadt; Rolf Gericke, Seeheim; Rolf Bergmann, Reichelsheim; Jacques De Peyer, Pfungstadt; Ingeborg Lues, Darmstadt, all of Fed. Rep. of Germany

[73] Assignee: Merck Patent Gesellschaft mit beschränkter Haftung, Darmstadt, Fed. Rep. of Germany

[21] Appl. No.: 440,622

[22] Filed: Nov. 22, 1989

[30] Foreign Application Priority Data

Nov. 26, 1988 [DE] Fed. Rep. of Germany ....... 3840011

[51] Int. Cl.$^5$ ................. C07D 413/04; C07D 413/12; A61K 31/535
[52] U.S. Cl. ................................. 514/230.5; 544/71; 544/90; 544/92
[58] Field of Search ........................... 544/71, 90, 92; 514/230.5

[56] References Cited

FOREIGN PATENT DOCUMENTS 56-43281 4/1981 Japan ................. 514/230.5
57-130979 8/1982 Japan .

OTHER PUBLICATIONS

Chemical Abstract 98:126129r (1982).
Tachikawa et al., "Studies on 1,3-Benzoxazines. III, Reaction of Imidoyl Chlorides . . . " Chem. Pharm. Bull. 29(12) 3529-3535 (1981).
Wachi et al., "Studies on 1,3-Benzoxazines. I, Syntheses of Primary 2-Amino-pyridines . . . " Chem. Pharm. Bull. 28(2) 465-472 (1980).
Chemical Abstract 95:115527s (1981).
Chemical Abstract 111:67818b (1988).

Primary Examiner—Mukund J. Shah
Assistant Examiner—Philip I. Datlow
Attorney, Agent, or Firm—Millen, White & Zelano

[57] ABSTRACT

Novel benzoxazine derivatives of the formula I

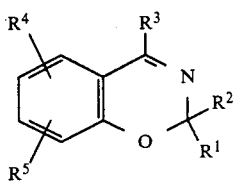

wherein $R^1$ to $R^5$ have the meanings defined herein, and salts thereof, exhibit effects on the cardiovascular system.

17 Claims, No Drawings

4-(PYRIDYL)- AND 4-(OXO-PYRIDYL)-1,3-BENZOXAZINES

SUMMARY OF THE INVENTION

The invention relates to novel benzoxazine derivatives of the formula I

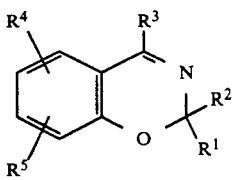

in which
R$^1$ and R$^2$ are each H or A, or, together, are alternatively alkylene having 3-6 C atoms,
R$^3$ is a pyridyl-Z-, pyridazinyl-Z-, pyrimidinyl-Z-, pyrazinyl-Z-, oxo-dihydro-pyridyl-(Z)$_n$-, oxo-dihydro-pyridazinyl-(Z)$_n$-, oxo-dihydro-pyrimidinyl-(Z)$_n$-, oxo-dihydro-pyrazinyl-(Z)$_n$-or oxo-dihydro-pyrrolyl-(Z)$_n$- radical, each of which is unsubstituted or monosubstituted or disubstituted by A, F, Cl, Br, I, OH, OA, OAc, SH, NO$_2$, NH$_2$, AcNH, HOOC and/or AOOC, it being possible for the radicals which are not bonded to the benzoxazine ring via Z to also be completely or partially hydrogenated,
R$^4$ and R$^5$ are each H, A, HO, AO, CHO, ACO, ACS, HOOC, AOOC, AO—CS, ACOO, A—C—S—O, hydroxyalkyl having 1-6 C atoms, mercaptoalkyl having 1-6 C atoms, NO$_2$, NH$_2$, NHA, NA$_2$, CN, F, Cl, Br, I, CF$_3$, ASO, ASO$_2$, AO—SO, AO—SO$_2$, AcNH, AO—CO—NH, H$_2$NSO, HANSO, A$_2$NSO, H$_2$NSO$_2$, HANSO$_2$, A$_2$NSO$_2$, H$_2$NCO, HANCO, A$_2$NCO, H$_2$NCS, HANCS, A$_2$NCS, ASONH, ASO$_2$NH, AOSONH, AOSO$_2$NH, ACO-alkyl, nitro-alkyl, cyanoalkyl, A—C(=NOH) or A—C(=NNH$_2$),
Z is O, S or NH,
n is 0 or 1,
A is alkyl having 1-6 C atoms,
-alkyl is alkylene having 1-6 C atoms, and
Ac is alkanoyl having 1-8 C atoms or aroyl having 7-11 C atoms,
with the proviso that R$^3$ is 2-oxopyrrolidino or 2-oxopiperidino and, simultaneously, R$^4$ is H only when R$^5$ is different from H, A, AO, F, Cl, Br and I, and salts thereof.

In the foregoing, selection of variables defined together is made independently.

Similarly compounds are known from JP 57,130,979.

The invention has the object of providing novel compounds having valuable properties, in particular those which can be used for the preparation of medicaments.

Upon further study of the specification and appended claims, further objects and advantages of this invention will become apparent to those skilled in the art.

It has been found that the compounds of the formula I and physiologically acceptable salts thereof have valuable pharmacological properties and good tolerability. Thus, they exhibit actions on the cardiovascular system, it generally being possible to observe a selective attack on the coronary system at relatively low doses and an antihypertensive effect at relatively high doses. Examples of effects on the coronary system are a decrease in resistance and increase in the flow, while the effect on the heart rate remains low. In addition, the compounds exhibit a relaxant action on various smooth-muscular organs (gastrointestinal tract, respiratory system and uterus). The actions of the compounds can be determined using methods which are known per se, as described, for example in EP-A-76,075, EP-A-168,619, EP-A-173,848 or AU-A-45,547/85 (Derwent Farmdoc. No. 86081769) and by K. S. Meesmann et al., Arzenimittelforschung 25 (11), 1975, 1770-1776. Examples of suitable experimental animals are mice, rats, guinea pigs, dogs, cats, monkeys or pigs.

The compounds can therefore be used as active compounds for medicaments in human and veterinary medicine. Furthermore, they can be used as intermediates for the preparation of further active compounds for medicaments.

In the formulae indicated, A is preferably an unbranched alkyl group having 1-6, preferably 1-4, in particular 1, 2 or 3 C atoms, in particular preferably methyl, furthermore preferably ethyl, propyl, isopropyl, butyl, isobutyl, in addition preferably sec.-butyl, tert.-butyl, pentyl, isopentyl (3-methylbutyl), hexyl or isohexyl (4-methylpentyl).

If R$^1$ and R$^2$ together are alkylene, the alkylene group is preferably unbranched, and in particular is preferably —(CH$_2$)$_n$—, where n is 3, 4, 5 or 6.

The group "-alkyl" is preferably —CH$_2$— or —CH$_2$CH$_2$—.

Ac is preferably alkanoyl having 1-6, in particular 1, 2, 3 or 4, C atoms, in particular preferably formyl or acetyl, in addition preferably propionyl, butyryl, isobutyryl, pentanoyl or hexanoyl, furthermore preferably benzoyl, o-, m- or p-toluyl, or 1- or 2-naphthoyl.

R$^1$ and R$^2$ are each preferably alkyl, in particular are each methyl or ethyl, and are preferably each methyl.

R$^3$ is preferably unsubstituted 2-oxo-1,2-dihydro-1-pyridyl (1H-2-pyridon-1-yl), 3-hydroxy-6-oxo-1,6-dihydro-pyridazin-1-yl or 2-oxo-4-hydroxy-1,2-dihydro-1-pyridyl, furthermore unsubstituted 2-oxo-1,2-dihydro-pyrazin-1-yl, 6-oxo-1,6-dihydro-pyridazin-1-yl, 2-oxo-1,2-dihydro-pyrimidin-1-yl, 6-oxo-1,6-dihydro-pyrimidin-1-yl, 2-oxo-2,3- or -2,5-dihydro-pyrrol-1-yl or 2-mercapto-pyridyl (=2-thioxo-1,2-dihydro-pyridin-1-yl). If R$^3$ is a substituted pyridone or thiopyridone ring, this ring is preferably monosubstituted in the 3-, 4- or 5-position or disubstituted in the 3- and 5-positions. Particularly preferred substituents are OH, NO$_2$ and NH$_2$, furthermore AOOC, OA, Cl, Br and NHCOCH$_3$, and particularly preferred substituted radicals R$^3$ are in particular 4- and furthermore 3-, 5- and 6-hydroxy-, 3-, 4-, 5- or 6-methoxy-, 3-, 4-, 5- or 6-acetoxy-, 3-, 5- or 6-chloro-, 3- or 5-nitro-, 3- or 5-amino-, 3- or 5-carboxy-, 3- or 5-methoxycarbonyl-, 3- or 5-ethoxycarbonyl-, 3- or 5-acetamido-, 3,5-dichloro-, 3,5-dibromo-, 3-chloro-5-nitro-, 3-nitro-5-chloro-, 3-bromo-5-nitro, 3-nitro-5-bromo-, 3,5-dinitro-, 3-chloro-5-amino-, 3-amino-5-chloro-, 3-bromo-5-amino-, 3-amino-5-bromo-, 3-chloro-5-acetamido-, 3-acetamido-5-chloro-, 3-bromo-5-acetamido- and 3-acetamido-5-bromo-2-oxo-1,2-dihydro-1-pyridyl or -2-thioxo-1,2-dihydro-1-pyridyl, 4- or 5-hydroxy-6-oxo-1,6-dihydro-pyridazin-1-yl, 3-, 4- or 5-methoxy-6-oxo-1,6-dihydro-pyridazin-1-yl, 3-, 4- or 5-ethoxycarbonyl-6-oxo-1,6-dihydro-pyrimidin-1-yl, or 2- or 4-hydroxy-6-oxo-1,6-dihydro-pyrimidin-1-yl.

Z is preferably O, furthermore S or NH.

R³ can furthermore preferably be: 2-oxo-1,2,3,4-tetrahydro-1-pyridyl, 2-oxo-1,2,3,6-tetrahydro-1-pyridyl, 2-oxo-1,2,5,6-tetrahydro-1-pyridyl, 2-oxo-hexahydro-1-pyridyl (=2-piperidinon-1-yl), 2-oxo-4-hydroxy-1,2,3,4-tetrahydro-1-pyridyl, 2-oxo-4-hydroxy-1,2,3,6-tetrahydro-1-pyridyl, 2-oxo-4-hydroxy-1,2,5,6-tetrahydro-1-pyridyl, 2-oxo-4-hydroxy-hexahydro-1-pyridyl, 6-oxo-1,2,3,6-tetrahydro-pyridazin-1-yl, 6-oxo-1,2,5,6-tetrahydro-pyridazin-1-yl, 6-oxo-1,4,5,6-tetrahydro-pyridazin-1-yl, 6-oxo-hexahydro-pyridazin-1-yl, 3-hydroxy-6-oxo-1,2,3,6-tetrahydro-pyridazin-1-yl, 3-hydroxy-6-oxo-1,2,5,6-tetrahydro-pyridazin-1-yl, 3-hydroxy-6-oxo-1,4,5,6-tetrahydro-pyridazin-1-yl, 3-hydroxy-6-oxo-hexahydro-pyridazin-1-yl, 2-oxo-1,2,3,4-tetrahydro-pyrimidin-1-yl, 2-oxo-1,2,3,6-tetrahydro-pyrimidin-1-yl, 2-oxo-1,2,5,6-tetrahydro-pyrimidin-1-yl, 2-oxo-hexahydro-pyrimidin-1-yl, 6-oxo-1,2,3,6-tetrahydro-pyrimidin-1-yl, 6-oxo-1,2,5,6-tetrahydro-pyrimidin-1-yl, 6-oxo-1,4,5,6-tetrahydro-pyrimidin-1-yl, 6-oxo-hexahydro-pyrimidin-1-yl, 2-oxo-1,2,3,4-tetrahydro-pyrazin-1-yl, 2-oxo-hexahydro-pyrazin-1-yl, 3-oxo-1,2,3,4-tetrahydro-pyrazin-1-yl, 3-oxo-hexahydro-pyrazin-1-yl or 2-oxo-tetrahydropyrrol-1-yl (=2-pyrrolidinon-1-yl).

If the radical R³ contains a Z group, the radical is preferably 6-hydroxy-3-pyridazinyl-oxy (=1,6-dihydro-6-oxo-3-pyridazinyl-oxy) or 2-hydroxy-4-pyridyl-oxy (=1,2-dihydro-2-oxo-4-pyridyl-oxy), furthermore preferably unsubstituted 2-, 3- or 4-pyridyl-oxy, 2-, 4- or 5-pyrimidinyl-oxy, 3-, 4- or 5-pyridazinyl-oxy or pyrazinyl-oxy; hydroxy-pyridyl-oxy, such as 3-, 4-, 5- or 6-hydroxy-2-pyridyl-oxy, 2-, 4- or 5-hydroxy-3-pyridyl-oxy, 3-hydroxy-4-pyridyl-oxy, 2-hydroxy-5-pyridyl-oxy; hydroxy-pyridazinyl-oxy, such as 4- or 5-hydroxy-3-pyridazinyl-oxy, 3-, 5- or 6-hydroxy-4-pyridazinyl-oxy; hydroxy-pyrimidinyl-oxy, such as 4- or 5-hydroxy-2-pyrimidinyl-oxy, pyrimidinyl-oxy, 2-, 5- or 6-hydroxy-4-pyrimidinyl-oxy, 2- or 4-hydroxy-5-pyrimidinyl-oxy; hydroxy-pyrazinyl-oxy, such as 3-, 5- or 6-hydroxy-2-pyrazinyl-oxy; dihydro-alkyloxo-pyridyl-oxy, such as 1,2-dihydro-1-methyl-2-oxo-3-, -4-, -5- or -6-pyridyl-oxy, 1,2-dihydro-1-ethyl-2-oxo-3-, -4-, -5- or -6-pyridyl-oxy; dihydro-alkyl-oxo-pyridazinyl-oxy, such as 1,6-dihydro-1-methyl-6-oxo-3, -4- or -5-pyridazinyl-oxy, 1,6-dihydro-1-ethyl-6-oxo-3-, -4- or -5-pyridazinyl-oxy; alkoxy-pyridyl-oxy, such as 3-, 4-, 5- or 6-methoxy-2-pyridyl-oxy, 2-, 4- or 5-methoxy-3-pyridyl-oxy, 2- or 3-methoxy-4-pyridyl-oxy, 2-methoxy-5-pyridyl-oxy, 2- or 3-ethoxy-4-pyridyl-oxy; alkoxy-pyridazinyl-oxy, such as 4-, 5- or 6-methoxy-3-pyridazinyl-oxy, 4-, 5- or 6-ethoxypyridazinyl-oxy, 3-, 5- or 6-methoxy-4-pyridazinyl-oxy, 3-, 5- or 6-ethoxy-4-pyridazinyl-oxy; alkoxy-pyrimidinyl-oxy, such as 4- or 5-methoxy-2-pyrimidinyl-oxy, 2-, 5- or 6-methoxy-4-pyrimidinyl-oxy, 2- or 4-methoxy-5-pyrimidinyl-oxy; alkoxy-pyrazinyl-oxy, such as 3-, 5- or 6-methoxy-2-pyrazinyl-oxy; amino-pyridyl-oxy, such as 3-, 4-, 5- or 6-aminopyridyl-oxy, 2-, 4- or 5-amino-3-pyridyl-oxy, 2- or 3-amino-4-pyridyl-oxy, 2-amino-5-pyridyl-oxy; amino-pyridazinyl-oxy, such as 4-, 5- or 6-amino-3-pyridazinyl-oxy, 3-, 5- or 6-amino-4-pyridazinyl-oxy; amino-pyrimidinyl-oxy, such as 4- or 5-amino-2-pyrimidinyl-oxy, 2-, 5- or 6-amino-4-pyrimidinyl-oxy, 2- or 4-amino-5-pyrimidinyl-oxy; amino-pyrazinyl-oxy, such as 3-, 5- or 6-amino-2-pyrazinyl-oxy; mercapto-pyridyl-oxy, such as 3-, 4-, 5- or 6-mercapto-2-pyridyl-oxy, 2-, 4- or 5-mercapto-3-pyridyl-oxy, 2- (=1,2-dihydro-2-thioxo-4-pyridyl-oxy) or 3-mercapto-4-pyridyl-oxy, 2-mercapto-5-pyridyl-oxy; mercapto-pyridazinyl-oxy, such as 4-, 5- or 6-mercapto-3-pyridazinyl-oxy (=1,6-dihydro-6-thioxo-3-pyridazinyl-oxy), 3-, 5- or 6-mercapto-4-pyridazinyl-oxy; mercapto-pyrimidinyl-oxy, such as 4- or 5-mercapto-2-pyrimidinyl-oxy, 2-, 5- or 6-mercapto-4-pyrimidinyl-oxy, 2- or 4-mercapto-5-pyrimidinyl-oxy; or mercapto-pyrazinyl-oxy, such as 3-, 5- or 6-mercapto-2-pyrazinyl-oxy.

Those radicals R³ which contain a hydroxyl or mercapto group adjacent to a ring N atom can also be in the tautomeric lactam or thiolactam form, as indicated above in individual cases.

In R⁴ and R⁵, the symbols preferably have the following meanings:

| | |
|---|---|
| A: | methyl, furthermore ethyl; |
| AO: | methoxy, furthermore ethoxy; |
| ACO: | acetyl, furthermore propionyl; |
| ACS: | thioacetyl, furthermore thiopropionyl; |
| AOOC: | methoxycarbonyl, furthermore ethoxycarbonyl; |
| AO—CS: | methoxy-thiocarbonyl, furthermore ethoxythiocarbonyl; |
| ACOO: | acetoxy, furthermore propionoxy; |
| ACSO: | thio(no)acetoxy, furthermore thio(no)propionoxy; |
| hydroxyalkyl: | hydroxymethyl or 1- or 2-hydroxyethyl; |
| mercaptoalkyl: | mercaptomethyl or 1- or 2-mercaptoethyl; |
| NHA: | methylamino, furthermore ethylamino; |
| NA₂: | dimethylamino, furthermore diethylamino; |
| ASO: | methylsulfinyl, furthermore ethylsulfinyl; |
| ASO₂: | methylsulfonyl, furthermore ethylsulfonyl; |
| AO—SO: | methoxy-sulfinyl, furthermore ethoxysulfinyl; |
| AO—SO₂: | methoxy-sulfonyl, furthermore ethoxysulfonyl; |
| Ac—NH: | acetamido, furthermore formamido, propionamido or benzamido; |
| AO—CO—NH: | methoxycarbonylamino, furthermore ethoxycarbonylamino; |
| HANSO: | methylaminosulfinyl, furthermore ethylaminosulfinyl; |
| A₂NSO: | dimethylaminosulfinyl, furthermore diethylaminosulfinyl; |
| HANSO₂: | methylaminosulfonyl, furthermore ethylaminosulfonyl; |
| A₂NSO₂: | dimethylaminosulfonyl, furthermore diethylaminosulfonyl; |
| HANCO: | N-methylcarbamoyl, furthermore N-ethylcarbamoyl; |
| A₂NOC: | N,N-dimethylcarbamoyl, furthermore N,N-diethylcarbamoyl; |
| HANCS: | N-methyl-thiocarbamoyl, furthermore N-ethyl-thiocarbamoyl; |
| A₂NCS: | N,N-dimethyl-thiocarbamoyl, furthermore N,N-diethyl-thiocarbamoyl; |
| ASONH: | methylsulfinylamino, furthermore ethylsulfinylamino; |
| ASO₂NH: | methylsulfonylamino, furthermore ethylsulfonylamino; |
| AOSONH: | methoxysulfinylamino, furthermore ethoxysulfinylamino; |
| AOSO₂NH: | methoxysulfonylamino, furthermore ethoxysulfonylamino; |
| ACO-alkyl: | 2-oxopropyl, 2-oxobutyl, 3-oxobutyl, 3-oxopentyl; |
| nitroalkyl: | nitromethyl, 1- or 2-nitroethyl; |
| cyanoalkyl | cyanomethyl, 1- or 2-cyanoethyl; |
| A—C(=NOH) | 1-oximinoethyl, furthermore 1-oximinopropyl; |
| A—C(=NNH₂): | 1-hydrazonoethyl, furthermore 1-hydrazonopropyl |

The radicals R⁴ and R⁵ are preferably in the 6- and 7-positions of the benzoxazine system. However, they can also be in the 5- and 6-, 5- and 7-, 5- and 8-, 6- and 8- and 7- and 8-positions.

Of the radicals R⁴ and R⁵, it is preferred that one is H while the other is different from H. This other radical is preferably in the 6-position, but can also be in the 5-, 7- or 8-position, and is preferably CN, BR or $NO_2$, furthermore preferably CHO, ACO (in particular acetyl), AOOC (in particular methoxycarbonyl or ethoxycarbonyl), ACOO (in particular acetoxy), and in addition preferably F, Cl, I, $CF_3$, $H_2NCO$, $H_2NCS$ or $NH_2$.

Accordingly, the invention relates, in particular, to those compounds of the formula I in which at least one of the radicals mentioned has one of the abovementioned preferred meanings. Some preferred groups of compounds may be expressed by the formulae Ia to Ii below, which conform to the formula I and in which the radicals not designated in greater detail are as defined in the formula I, but in which

| | |
|---|---|
| in Ia | $R^1$ and $R^2$ are each A; |
| in Ib | $R^1$ and $R^2$ are each $CH_3$; |
| in Ic | $R^1$ and $R^2$ together are alkylene having 3–6 C atoms; |
| in Id | $R^3$ is 2-oxo-1, 2-dihydro-1-pyridyl, 2-oxo-4-hydroxy-1, 2-dihydro-1-pyridyl or 3-hydroxy-6-oxo-1, 6-dihydro-1-pyridazinyl; |
| in Ie | $R^3$ is 2-pyridyloxy, 2-hydroxy-4-pyridyloxy or 6-hydroxy-3-pyridazinyloxy; |
| in If | $R^3$ is 2-oxo-1, 2-dihydro-1-pyridyl; |
| in Ig | $R^1$ and $R^2$ are each $CH_3$ and $R^3$ is 2-oxo-1, 2-dihydro-1-pyridyl, 2-oxo-4-hydroxy-1, 2-dihydro-1-pyridyl or 3-hydroxy-6-oxo-1, 6-dihydro-pyridazinyl; |
| in Ih | $R^1$ and $R^2$ are each $CH_3$ and $R^3$ is 2-pyridyloxy, 2-hydroxy-4-pyridyloxy or 6-hydroxy-3-pyridazinyloxy; |
| in Ii | $R^1$ and $R^2$ are each $CH_3$ and $R^3$ is 2-oxo-1, 2-dihydro-1-pyridyl. |

Furthermore, preferred compounds are those of the formulae I and Ia to Ii in which in each case, in addition, (a)

$R^4$ is different from H and
$R^5$ is H;

(b)

$R^4$ is different from H and is in the 6-position and
$R^5$ is H;

(c)

$R^4$ is $NO_2$, CN, CHO, ACO, HOOC, AOOC, ACOO, F, Cl, Br, I, $CF_3$, $H_2NCO$, $H_2NCS$ or $NH_2$ and
$R^5$ is H;

(d)

$R^4$ is $NO_2$, CN, CHO, ACO, HOOC, AOOC, ACOO, F, Cl, Br, I, $CF_3$, $H_2NCO$, $H_2NCS$ or $NH_2$ and is in the 6-position and
$R^5$ is H;

(e)

$R^4$ is $NO_2$, CN, CHO, $CH_3CO$, $CH_3OOC$, $C_2H_5OOC$, $CH_3COO$ or Br and
$R^5$ is H;

(f)

$R^4$ is $NO_2$, CN, CHO, $CH_3CO$, $CH_3OOC$, $C_2H_5OOC$, $CH_3COO$ or Br and is in the 6-position and
$R^5$ is H;

(g)

$R^4$ is Br, $NO_2$ or CN and
$R^5$ is H;

(h)

$R^4$ is Br, $NO_2$ or CN and is in the 6-position and
$R^5$ is H;

(i)

$R^4$ is CN and
$R^5$ is H;

(j)

$R^4$ is CN and is in the 6-position and
$R^5$ is H.

In addition, the radicals $R^1$ to $R^5$, Z, A, "-alkyl" and Ac above and below are as defined in the case of formula I, unless expressly stated otherwise.

The invention furthermore relates to a process for the preparation of benzoxazine derivatives of the formula I, characterized in that a benzoxazine of the formula II

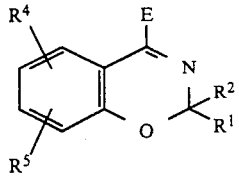

II in which
E is Cl, Br, I or a reactively esterified OH group and
$R^1$, $R^2$, $R^4$, and $R^5$ are as defined in the case of formula I, is reacted with a compound of the formula III $R^3$—H     III in which $R^3$ is as defined in the case of formula I, or with a reactive derivative thereof,
and/or in that, in a compound of the formula I, one or more of the radicals $R^3$, $R^4$ and/or $R^5$ are converted into other radicals $R^3$, $R^4$ and/or $R^5$, and/or in that a basic compound of the formula I is converted into one of its acid-addition salts by treatment with an acid.

In addition, the compounds of the formula I are prepared by methods which are known per se, as described in the literature (e.g. in the standard works such as Houben-Weyl, Methoden der organischen Chemie [Methods of Organic Chemistry], Georg-Thieme-Verlag, Stuttgart; Organic Reactions, John Wiley & Sons, Inc., New York; and in the abovementioned patent applications), and under reaction conditions which are known and suitable for the reactions mentioned. Use can also be made here of variants which are known per se, but are not described in detail here.

If desired, the starting materials can also be formed in situ by not isolating them from the reaction mixture, but instead immediately reacting them further to form the compounds of the formula I.

The compounds of the formula I are preferably prepared by reacting compounds of the formula II with compounds of the formula III, preferably in the presence of an inert solvent at temperatures between about 0° and 150°. In this reaction, depending on the reaction conditions and constitution of the starting materials, compounds of the formula I which are connected to the benzoxazine ring via the N atom [e.g. 4-(2-oxo-1,2-dihydro-pyridyl)-2H-1,3-benzoxazines] or via an O bridge [e.g. 4-(2-pyridyl-oxy)-2H-1,3-benzoxazines] are produced alongside one another when starting materials of the formula III which contain a —CO—NH— group (e.g. 1H-2-pyridone) are used.

Starting materials of the formula II where E=Cl are preferred. They can be obtained, for example, by condensing salicylamides which are optionally substituted by the radicals $R^4$ and $R^5$ with aldehydes or ketones of the formula $R^1$—CO—$R^2$ to form the corresponding 2-$R^1$-2-$R^2$-2H-1,3-benzoxazin-4-ones and subsequent reaction with $POCl_3/PCl_5$.

In compounds of the formula II, possible "reactive esterified OH groups" are, in particular, alkylsulfonyloxy having 1-6 C atoms (e.g. methanesulfonyloxy) and arylsulfonyloxy having 6-10 C atoms (e.g. benzenesulfonyloxy, p-toluenesulfonyloxy, or 1- or 2-naphthalenesulfonyloxy).

The starting materials of the formula III are known in general terms.

Suitable reactive derivatives of III are the appropriate salts, e.g. the Na or K salts, which can also be formed in situ.

It is preferable to carry out the reaction of II with III in the presence of a base. Examples of suitable bases are the hydroxides, carbonates, alcoholates, hydrides or alternatively amides of alkali metals or alkaline earth metals, such as NaOH, KOH, Ca(OH)$_2$, Na$_2$CO$_3$, K$_2$CO$_3$, Na methylate, ethylate or tert.-butylate, K methylate, ethylate or tert.-butylate, NaH, KH, CaH$_2$ NaNH$_2$ or KNH$_2$, furthermore organic bases, such as triethylamine or pyridine, which can also be used in excess and can then simultaneously serve as solvent.

Suitable inert solvents are, in particular, alcohols, such as methanol, ethanol, isopropanol, n-butanol or tert.-butanol; ethers, such as diethyl ether, diisopropyl ether, tetrahydrofuran or dioxane; glycol ethers, such as ethylene glycol monomethyl or monoethyl ether (methyl glycol or ethyl glycol), ethylene glycol dimethyl ether (diglyme); ketones, such as acetone or butanone; nitriles, such as acetonitrile; nitro compounds, such as nitromethane or nitrobenzene; esters, such as ethyl acetate; amides, such as dimethylformamide (DMF), dimethylacetamide or hexamethylphosphoric triamide; sulfoxides, such as dimethyl sulfoxide (DMSO); chlorinated hydrocarbons, such as dichloromethane, chloroform, trichloroethylene, 1,2-dichloroethane or carbon tetrachloride; or hydrocarbons, such as benzene, toluene or xylene. Mixtures of these solvents with one another are also suitable.

In addition, one or more of the radicals $R^3$, $R^4$ and/or $R^5$ in a compound of the formula I can be converted into another radical $R^3$, $R^4$ and/or $R^5$.

For example, it is possible to replace a H atom by a halogen atom by means of a halogenation or by a nitro group by means of a nitration and/or to reduce a nitro group to an amino group and/or to alkylate or acylate an amino or hydroxyl group and/or to convert a cyano group (e.g. using HCl in water/methanol at 20°-100°) to a carboxyl group or (e.g. using Raney nickel in water/acetic acid/pyridine in the presence of sodium phosphate) to a formyl group or (e.g. using KOH in tert.-butanol) to a carbamoyl group or (e.g. using H$_2$S in pyridine/triethylamine) to a thiocarbamoyl group and/or to convert a —CO—NH— group (e.g. using P$_2$S$_5$ or using Lawesson reagent in toluene) to a —CS—NH— or a —C(SH)=N— group.

Nitration succeeds under customary conditions, for example using a mixture of concentrated HNO$_3$ and concentrated H$_2$SO$_4$ at temperatures between 0° and 30°. If at least one of the substituents $R^4$ and $R^5$ is an electronegative group such as CN or NO$_2$, the nitration takes place predominantly on the radical $R^3$; if it is not the case, mixtures are generally obtained in which the nitro groups can be on the radical $R^3$ or on the benzene ring.

An analogous situation applies to halogenation, which can be carried out, for example, using elemental chlorine or bromine in one of the customary inert solvents at temperatures between about 0° and 30°.

A primary or secondary amino group and/or an OH group can be converted to the corresponding secondary or tertiary amino group and/or alkoxy group by treatment with alkylating agents. Examples of suitable alkylating agents are compounds of the formulae A—Cl, A—Br or A—I or appropriate sulfuric acid esters or sulfonic acid esters, such as methyl chloride, methyl bromide, methyl iodide, dimethyl sulfate and methyl p-toluenesulfonate. Furthermore, for example, one or two methyl groups can be introduced using formaldehyde in the presence of formic acid. The alkylation is preferably carried out in the presence or absence of one of the inert solvents mentioned, for example DMF, at temperatures between about 0° and about 120°, it also being possible for a catalyst to be present, preferably a base, such as potassium tert.-butylate or NaH.

Suitable acylating agents for acylating amino or hydroxyl groups are preferably the halides (e.g. chlorides or bromides) or anhydrides of carboxylic acids of formula Ac—OH, for example acetic anhydride, propionyl chloride, isobutyryl bromide, formic acid/acetic anhydride, or benzoyl chloride. The addition of a base, such as pyridine or triethylamine, during the acylation is possible. The acylation is preferably carried out in the presence or absence of an inert solvent, for example a hydrocarbon such as toluene, a nitrile such as acetonitrile, an amide such as DMF or an excess of a tertiary base, such as pyridine or triethylamine, at temperatures between about 0° and about 160°, preferably between 20° and 120°. Formylation also succeeds using formic acid in the presence of pyridine.

It is possible to convert a base of the formula I into the pertinent acid-addition salt using an acid. Suitable acids for this reaction are, in particular, those which give physiologically acceptable salts. Thus, inorganic acids can be used, for example sulfuric acid, nitric acid, hydrohalic acids, such as hydrochloric acid or hydrobromic acid, phosphoric acids, such as orthophosphoric acid, or sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methanesulfonic acid, ethanesulfonic acid, ethanedisulfonic acid, 2-hydroxyethanesulfonic acid, benzenesulfonic acid, p-toluenesulfonic acid, naphthalene mono-and di-sulfonic acids, or laurylsulfuric acid. Salts with physiologically unacceptable acids, for example picrates, can be used to purify the compounds of the formula I.

The compounds of the formula I may have one or more chiral centers. When prepared, they can therefore be obtained as racemates or, if optically active starting materials are used, also in optically active form. If the compounds have two or more chiral centers, they can when synthesized be produced as mixtures of racemates from which the individual racemates can be isolated in pure form, for example by recrystallization from inert solvents. If desired, the racemates obtained can be resolved into their enantiomers mechanically or chemically by methods which are known per se. Thus, diastereomers can be formed from the racemate by reaction with an optically active resolving agent. Examples of suitable resolving agents for basic compounds of the formula I are optically active acids, such as the D- and L-forms of tartaric acid, dibenzoyltartaric acid, diacetyltartaric acid, camphorsulfonic acids, mandelic acid, malic acid or lactic acid. The various forms of the diastereomers can be resolved in a manner known per se, for example by fractional crystallization, and the enantiomers of the formula I can be liberated from the diastereomers in a manner known per se. Enantiomers can furthermore be resolved by chromatography on optically active support materials.

The compounds of the formula I and their physiologically acceptable salts can be used to prepare pharmaceutical preparations, in particular by non-chemical methods. In this case, they can be converted into a suitable dosage form together with at least one solid, liquid and/or semi-liquid carrier or adjuvant and optionally in combination with one or more further active compound(s).

The invention furthermore relates to agents, in particular pharmaceutical preparations which contain at least one compound of the formula I and/or a physiologically acceptable salt thereof. These preparations can be used as medicaments in human or veterinary medicine. Suitable carrier materials are organic or inorganic substances which are suitable for enteral (for example oral), parenteral or topical application and which do not react with the novel compounds, for example water, vegetable oils, benzyl alcohols, polyethylene glycols, glycerol triacetate, gelatin, carbohydrates, such as lactose or starch, magnesium stearate, talc, lanolin or vaseline. Tablets, coated tablets, capsules, syrups, juices or drops are particularly suitable for oral administration, suppositories for rectal administration, solutions, preferably oily or aqueous solutions, and furthermore suspensions, emulsions or implantates for parenteral administration, and ointments, creams, pastes, lotions, gels, sprays, foams, aerosols, solutions (for example solutions in alcohols, such as ethanol or isopropanol, acetonitrile, DMF, dimethylacetamide, 1,2-propanediol or mixtures thereof with one another and/or with water) or powders for topical application. The novel compounds can also be lyophilized, and the lyophilizates obtained can be used, for example, to prepare injection preparations. Liposomal preparations are also suitable, in particular for topical application. The preparations indicated may be sterilized and/or contain adjuvants, such as lubricants, preservatives, stabilizers and/or wetting agents, emulsifiers, salts for affecting the osmotic pressure, buffers, colorants, flavorings and/or perfumes. If desired, they can also contain one or more further active compounds, for example one or more vitamins.

The compounds of the formula I and the physiologically acceptable salts thereof can be administered to humans or animals, in particular mammals, such as monkeys, dogs, cats, rats or mice, and used in the therapeutic treatment of the human or animal body and also in combating diseases, in particular in the therapy and/or prophylaxis of disturbances of the cardiovascular system, in particular decompensated heart insufficiency, Angina pectoris, arrhythmia, peripheral or cerebral vascular disorders, and states of illness associated with high blood pressure, furthermore of diseases associated with changes in the non-vascular muscles, for example asthma and incontinence of the bladder.

In the course of these treatments, the substances according to the invention are generally administered analogously to known antiangina agents or antihypertensives, for example nicorandil or cromakalim, preferably in doses between about 0.01 and 5 mg, in particular between 0.02 and 0.5 mg, per dosage unit. The daily dose is preferably between about 0.0001 and 0.1, in particular between 0.0003 and 0.01, mg/kg of body weight. However, the specific dose for each particular patient depends on a very wide variety of factors, for example on the efficacy of the specific compound employed, on the age, body weight, general state of health, sex, on the cost, on the time and method of administration, on the rate of excretion, medicament combination and severity of the particular disease to which the therapy applies. Oral administration is preferred.

The compounds of the formula I and salts thereof are furthermore suitable, in particular on topical application, for the treatment of alopecia, including androgenic alopecia and Alopecia areata. In particular, pharmaceutical preparations which are suitable for topical treatment of the scalp and are mentioned above are used for this purpose. They contain about 0.005 to 10, preferably 0.5 to 3, % by weight of at least one compound of the formula I and/or at least one salt thereof. In addition, these compounds can be used against alopecia analogously to the data in WO 88/00822.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding application German P 38 40 011.1, filed Nov. 26, 1988, are hereby incorporated by reference.

EXAMPLES

In the examples below, "customary work-up" means:

Water is added, if necessary, the mixture is extracted with an organic solvent, such as ethyl acetate, the phases are separated, the organic phase is dried over sodium sulfate, filtered and evaporated, and the residue is purified by chromatography and/or crystallization.

Above and below, all temperatures are given in °C.

EXAMPLE 1

1.9 g of 1H-2-pyridone are added to a stirred slurry of 741 mg of NaH (80%) in 40 ml of dry DMF while passing $N_2$ into the flask. After the mixture has been stirred for 0.5 hour, 2.2 g of 2,2-dimethyl-4-chloro-6-cyano-2H-1,3-benzoxazine ("IIa"; m.p. 127°–129°; obtainable by condensing 5-cyano-2-hydroxybenzamide with acetone to form 2,2-dimethyl-6-cyano-3,4-dihydro-2H-1,3-benzoxazin-4-one (m.p. 213°-216°) and subsequently reacting the product with POCl₃/PCl₅ are added, and the mixture is stirred at 50° for a further 72 hours. Saturated NaCl solution is subsequently added, the mixture is extracted with ethyl acetate, the organic phase is washed with NaCl solution, dried over sodium sulfate and evaporated, and the residue is chromatographed on silica gel (ethyl acetate/petroleum ether). 2,2-Dimethyl-4-(2-pyridyl-oxy)-6-cyano-2H-1,3-benzoxazine ("A"; m.p. 115°-116°) is obtained as the first fraction, and 2,2-dimethyl-4-(2-oxo-1,2-dihydropyridyl)-6-cyano-2H-1,3-benzoxazine ("B"; m.p. 158°-159°) as the second fraction.

2,2-Dimethyl-4-(2-oxo-4-hydroxy-1,2-dihydro-1-pyridyl)-6-cyano-2H-1,3-benzoxazine and 2,2-dimethyl-4-(2-hydroxy-4-pyridyloxy)-6-cyano-2H-1,3-benzoxazine (m.p. 275°-278°) are obtained analogously using 2,4-dihydroxy-pyridine (=4-hydroxy-1H-2-pyridone).

2,2-Dimethyl-4-(3-hydroxy-6-oxo-1,6-dihydro-1-pyridazinyl)-6-cyano-2H-1,3-benzoxazine and 2,2-dimethyl-4-(6-hydroxy-3-pyridazinyl-oxy)-6-cyano-2H-1,3-benzoxazine, m.p. 189°-190°, are obtained analogously, using 3,6-dihydroxypridazine (=3-hydroxy-6-oxo-1,6-dihydro-pyridazine).

The following are obtained analogously:
2,2-dimethyl-4-(2-oxo-1,2-dihydro-1-pyridyl)-2H-1,3-benzoxazine, m.p. 144°-145°
2,2-dimethyl-4-(2-pyridyl-oxy)-2H-1,3-benzoxazine
2,2-dimethyl-4-(2-thioxo-1,2-dihydro-1-pyridyl)-6-cyano-2H-1,3-benzoxazine
2,2-dimethyl-4-(2-pyridyl-thio)-6-cyano-2H-1,3-benzoxazine
2,2-dimethyl-4-(2-oxo-3-chloro-1,2-dihydro-1-pyridyl)-6-cyano-2H-1,3-benzoxazine
2,2-dimethyl-4-(3-chloro-2-pyridyl-oxy)-6-cyano-2H-1,3-benzoxazine
2,2-dimethyl-4-(2-oxo-5-chloro-1,2-dihydro-1-pyridyl)-6-cyano-2H-1,3-benzoxazine
2,2-dimethyl-4-(5-chloro-2-pyridyl-oxy)-6-cyano-2H-1,3-benzoxazine
2,2-dimethyl-4-(2-oxo-6-chloro-1,2-dihydro-1-pyridyl)-6-cyano-2H-1,3-benzoxazine
2,2-dimethyl-4-(6-chloro-2-pyridyl-oxy)-6-cyano-2H-1,3-benzoxazine
2,2-dimethyl-4-(2-oxo-3-hydroxy-1,2-dihydro-1-pyridyl)-6-cyano-2H-1,3-benzoxazine
2,2-dimethyl-4-(3-hydroxy-2-pyridyl-oxy)-6-cyano-2H-1,3-benzoxazine
2,2-dimethyl-4-(2-oxo-5-hydroxy-1,2-dihydro-1-pyridyl)-6-cyano-2H-1,3-benzoxazine
2,2-dimethyl-4-(5-hydroxy-2-pyridyl-oxy)-6-cyano-2H-1,3-benzoxazine
2,2-dimethyl-4-(2-oxo-3-methoxy-1,2-dihydro-1-pyridyl)-6-cyano-2H-1,3-benzoxazine
2,2-dimethyl-4-(3-methoxy-2-pyridyl-oxy)-6-cyano-2H-1,3-benzoxazine
2,2-dimethyl-4-(2-oxo-3-acetoxy-1,2-dihydro-1-pyridyl)-6-cyano-2H-1,3-benzoxazine
2,2-dimethyl-4-(3-acetoxy-2-pyridyl-oxy)-6-cyano-2H-1,3-benzoxazine
2,2-dimethyl-4-(2-oxo-3-nitro-1,2-dihydro-1-pyridyl)-6-cyano-2H-1,3-benzoxazine
2,2-dimethyl-4-(3-nitro-2-pyridyl-oxy)-6-cyano-2H-1,3-benzoxazine
2,2-dimethyl-4-(2-oxo-5-nitro-1,2-dihydro-1-pyridyl)-6-cyano-2H-1,3-benzoxazine
2,2-dimethyl-4-(5-nitro-2-pyridyl-oxy)-6-cyano-2H-1,3-benzoxazine
2,2-dimethyl-4-(2-oxo-3-amino-1,2-dihydro-1-pyridyl)-6-cyano-2H-1,3-benzoxazine
2,2-dimethyl-4-(3-amino-2-pyridyl-oxy)-6-cyano-2H-1,3-benzoxazine
2,2-dimethyl-4-(2-oxo-5-amino-1,2-dihydro-1-pyridyl)-6-cyano-2H-1,3-benzoxazine
2,2-dimethyl-4-(5-amino-2-pyridyl-oxy)-6-cyano-2H-1,3-benzoxazine
2,2-dimethyl-4-(2-oxo-3-acetamido-1,2-dihydro-1-pyridyl)-6-cyano-2H-1,3-benzoxazine
2,2-dimethyl-4-(3-acetamido-2-pyridyl-oxy)-6-cyano-2H-1,3-benzoxazine
2,2-dimethyl-4-(2-oxo-5-acetamido-1,2-dihydro-1-pyridyl)-6-cyano-2H-1,3-benzoxazine
2,2-dimethyl-4-(5-acetamido-2-pyridyl-oxy)-6-cyano-2H-1,3-benzoxazine
2,2-dimethyl-4-(2-oxo-3-carboxy-1,2-dihydro-1-pyridyl)-6-cyano-2H-1,3-benzoxazine
2,2-dimethyl-4-(3-carboxy-2-pyridyl-oxy)-6-cyano-2H-1,3-benzoxazine
2,2-dimethyl-4-(2-oxo-3,5-dichloro-1,2-dihydro-1-pyridyl)-6-cyano-2H-1,3-benzoxazine
2,2-dimethyl-4-(3,5-dichloro-2-pyridyl-oxy)-6-cyano-2H-1,3-benzoxazine
2,2-dimethyl-4-(2-oxo-3,5-dibromo-1,2-dihydro-1-pyridyl)-6-cyano-2H-1,3-benzoxazine
2,2-dimethyl-4-(3,4-dibromo-2-pyridyl-oxy)-6-cyano-2H-1,3-benzoxazine
2,2-dimethyl-4-(2oxo-3-chloro-5-nitro-1,2-dihydro-1-pyridyl)-6-cyano-2H-1,3-benzoxazine
2,2-dimethyl-4-(3-chloro-5-nitro-2-pyridyl-oxy)-6-cyano-2H-1,3-benzoxazine
2,2-dimethyl-4-(2-oxo-3-nitro-5-chloro-1,2-dihydro-1-pyridyl)-6-cyano-2H-1,3-benzoxazine
2,2-dimethyl-4-(3-nitro-5-chloro-2-pyridyl-oxy)-6-cyano-2H-1,3-benzoxazine
2,2-dimethyl-4-(2-oxo-3-bromo-5-nitro-1,2-dihydro-1-pyridyl)-6-cyano-2H-1,3-benzoxazine
2,2-dimethyl-4-(3-bromo-5-nitro-2-pyridyl-oxy)-6-cyano-2H-1,3-benzoxazine
2,2-dimethyl-4-(2-oxo-3-nitro-5-bromo-1,2-dihydro-1-pyridyl)-6-cyano-2H-1,3-benzoxazine
2,2-dimethyl-4-(3-nitro-5-bromo-2-pyridyl-oxy)-6-cyano-2H-1,3-benzoxazine
2,2-dimethyl-4-(2-oxo-3,5-dinitro-1,2-dihydro-1-pyridyl)-6-cyano-2H-1,3-benzoxazine
2,2-dimethyl-4-(3,5-dinitro-2-pyridyl-oxy)-6-cyano-2H-1,3-benzoxazine
2,2-dimethyl-4-(2-oxo-3-chloro-5-amino-1,2-dihydro-1-pyridyl)-6-cyano-2H-1,3-benzoxazine
2,2-dimethyl-4-(3-chloro-5-amino-2-pyridyl-oxy)-6-cyano-2H-1,3-benzoxazine
2,2-dimethyl-4-(2-oxo-3-amino-5-chloro-1,2-dihydro-1-pyridyl)-6-cyano-2H-1,3-benzoxazine
2,2-dimethyl-4-(3-amino-5-chloro-2-pyridyl-oxy)-6-cyano-2H-1,3-benzoxazine
2,2-dimethyl-4-(2-oxo-3-bromo-5-amino-1,2-dihydro-1-pyridyl)-6-cyano-2H-1,3-benzoxazine
2,2-dimethyl-4-(3-bromo-5-amino-2-pyridyl-oxy)-6-cyano-2H-1,3-benzoxazine
2,2-dimethyl-4-(2-oxo-3-amino-5-bromo-1,2-dihydro-1-pyridyl)-6-cyano-2H-1,3-benzoxazine
2,2-dimethyl-4-(3-amino-5-bromo-2-pyridyl-oxy)-6-cyano-2H-1,3-benzoxazine
2,2-dimethyl-4-(2-oxo-3-chloro-5-acetamido-1,2-dihydro-1-pyridyl)-6-cyano-2H-1,3-benzoxazine 2,2-dimethyl-4-(3-chloro-5-acetamido-2-pyridyl-oxy)-6-cyano-2H-1,3-benzoxazine 2,2-dimethyl-4-(2-oxo-3-acetamido-5-chloro-1,2-dihydro-1-pyridyl)-6-cyano-2H-1,3-benzoxazine 2,2-dimethyl-4-(3-acetamido-5-chloro-2-pyridyl-oxy)-6-cyano-2H-1,3-benzoxazine 2,2-dimethyl-4-(2-oxo-3-bromo-5-acetamido-1,2-dihydro-1-pyridyl)-6-cyano-2H-1,3-benzoxazine 2,2-dimethyl-4-(3-bromo-5-acetamido-2-pyridyl-oxy)-6-cyano-2H-1,3-benzoxazine 2,2-dimethyl-4-(2-oxo-3-acetamido-5-bromo-1,2-dihydro-1-pyridyl)-6-cyano-2H-1,3-benzoxazine 2,2-dimethyl-4-(3-acetamido-5-bromo-2-pyridyl-oxy)-6-cyano-2H-1,3-benzoxazine 2,2-dimethyl-4-(2-oxo-1,2-dihydro-1-pyridyl)-6-acetyl-2H-1,3-benzoxazine 2,2-dimethyl-4-(2-pyridyl-oxy)-6-acetyl-2H-1,3-benzoxazine 2,2-dimethyl-4-(2-oxo-1,2-dihydro-1-pyridyl)-6-methoxycarbonyl-2H-1,3-benzoxazine 2,2-dimethyl-4-(2-pyridyl-oxy)-6-methoxycarbonyl-2H-1,3-benzoxazine 2,2-dimethyl-4-(2-oxo-1,2-dihydro-1-pyridyl)-6-ethoxycarbonyl-2H-1,3-benzoxazine 2,2-dimethyl-4-(2-pyridyl-oxy)-6-ethoxycarbonyl-2H-1,3-benzoxazine 2,2-dimethyl-4-(2-oxo-1,2-dihydro-1-pyridyl)-6-fluoro-2H-1,3-benzoxazine 2,2-dimethyl-4-(2-pyridyl-oxy)-6-fluoro-2H-1,3-benzoxazine 2,2-dimethyl-4-(2-oxo-1,2-dihydro-1-pyridyl)-6-chloro-2H-1,3-benzoxazine, m.p. 114°

2,2-dimethyl-4-(2-pyridyl-oxy)-6-chloro-2H-1,3-benzoxazine 2,2-dimethyl-4-(2-oxo-1,2-dihydro-1-pyridyl)-6-bromo-2H-1,3-benzoxazine, m.p. 134° (over 2,2-dimethyl-6-bromo-3,4-dihydro-2H-1,3-benzoxazin-4-one, m.p. 169°–175°, and 2,2-dimethyl-4-chloro-6-bromo-2H-1,3-benzoxazine, b.p. 150°–190°/1.3–2.7 mbar, air bath, bulb tube distillation)

2,2-dimethyl-4-(2-pyridyl-oxy)-6-bromo-2H-1,3-benzoxazine 2,2-dimethyl-4-(2-oxo-1,2-dihydro-1-pyridyl)-6-nitro-2H-1,3-benzoxazine 2,2-dimethyl-4-(2-pyridyl-oxy)-6-nitro-2H-1,3-benzoxazine 2,2-dimethyl-4-(2-oxo-1,2-dihydro-1-pyridyl)-6-trifluoromethyl-2H-1,3-benzoxazine 2,2-dimethyl-4-(2-pyridyl-oxy)-6-trifluoromethyl-2H-1,3-benzoxazine 2,2-dimethyl-4-(2-oxo-1,2-dihydro-1-pyridyl)-6-acetamido-2H-1,3-benzoxazine 2,2-dimethyl-4-(2-pyridyl-oxy)-6-acetamido-2H-1,3-benzoxazine 2,2-dimethyl-4-(2-oxo-1,2-dihydro-1-pyridyl)-7-cyano-2H-1,3-benzoxazine 2,2-dimethyl-4-(2-pyridyl-oxy)-7-cyano-2H-1,3-benzoxazine 2,2-dimethyl-4-(2-oxo-1,2-dihydro-1-pyridyl)-6-acetamido-7-nitro-2H-1,3-benzoxazine 2,2-dimethyl-4-(2-pyridyl-oxy)-6-acetamido-7-nitro-2H-1,3-benzoxazine 2-methyl-4-(2-oxo-1,2-dihydro-1-pyridyl)-6-cyano-2H-1,3-benzoxazine 2-methyl-4-(2-pyridyl-oxy)-6-cyano-2H-1,3-benzoxazine 2-methyl-2-ethyl-4-(2-oxo-1,2-dihydro-1-pyridyl)-6-cyano-2H-1,3-benzoxazine 2-methyl-2-ethyl-4-(2-pyridyl-oxy)-6-cyano-2H-1,3-benzoxazine 2,2-diethyl-4-(2-oxo-1,2-dihydro-1-pyridyl)-6-cyano-2H-1,3-benzoxazine 2,2-diethyl-4-(2-pyridyl-oxy)-6-cyano-2H-1,3-benzoxazine 2,2-tetramethylene-4-(2-oxo-1,2-dihydro-1-pyridyl)-6-cyano-2H-1,3-benzoxazine 2,2-tetramethylene-4-(2-pyridyl-oxy)-6-cyano-2H-1,3-benzoxazine 2,2-pentamethylene-4-(2-oxo-1,2-dihydro-1-pyridyl)-6-cyano-2H-1,3-benzoxazine 2,2-pentamethylene-4-(2-pyridyl-oxy)-6-cyano-2H-1,3-benzoxazine 2,2,3-trimethyl-4-(2-oxo-1,2-dihydro-1-pyridyl)-6-cyano-2H-1,3-benzoxazine 2,2,3-trimethyl-4-(2-pyridyl-oxy)-6-cyano-2H-1,3-benzoxazine 2,2-dimethyl-4-(6-oxo-1,6-dihydro-1-pyridazinyl)-6-cyano-2H-1,3-benzoxazine 2,2-dimethyl-4-(3-pyridazinyl-oxy)-6-cyano-2H-1,3-benzoxazine 2,2-dimethyl-4-(3-ethoxycarbonyl-6-oxo-1,6-dihydro-1-pyridazinyl)-6-cyano-2H-1,3-benzoxazine 2,2-dimethyl-4-(6-ethoxycarbonyl-3-pyridazinyl-oxy)-6-cyano-2H-1,3-benzoxazine 2,2-dimethyl-4-(2-oxo-1,2-dihydro-1-pyrimidinyl)-6-cyano-2H-1,3-benzoxazine 2,2-dimethyl-4-(2-pyrimidinyl-oxy)-6-cyano-2H-1,3-benzoxazine 2,2-dimethyl-4-(2-oxo-4-hydroxy-1,2-dihydro-1-pyrimidinyl)-6-cyano-2H-1,3-benzoxazine 2,2-dimethyl-4-(4-hydroxy-2-pyrimidinyl-oxy)-6-cyano-2H-1,3-benzoxazine 2,2-dimethyl-4-(6-oxo-1,6-dihydro-1-pyrimidinyl)-6-cyano-2H-1,3-benzoxazine 2,2-dimethyl-4-(4-pyrimidinyl-oxy)-6-cyano-2H-1,3-benzoxazine 2,2-dimethyl-4-(4-hydroxy-6-oxo-1,6-dihydro-1-pyrimidinyl)-6-cyano-2H-1,3-benzoxazine 2,2-dimethyl-4-(4-hydroxy-6-pyrimidinyl-oxy)-6-cyano-2H-1,3-benzoxazine 2,2-dimethyl-4-(2-oxo-1,2-dihydro-1-pyrazinyl)-6-cyano-2H-1,3-benzoxazine 2,2-dimethyl-4-(2-pyrazinyl-oxy)-6-cyano-2H-1,3-benzoxazine 2,2-dimethyl-4-(2-oxo-2,5-dihydro-1-pyrrolyl)-6-cyano-2H-1,3-benzoxazine 2,2-dimethyl-4-(2-pyrrolyl-oxy)-6-cyano-2H-1,3-benzoxazine 2,2-dimethyl-4-(2-oxo-4-hydroxy-1,2-dihydro-1-pyridyl)-6-bromo-2H-1,3-benzoxazine 2,2-dimethyl-4-(2-hydroxy-4-pyridyl-oxy)-6-bromo-2H-1,3-benzoxazine, m.p. 171°–172°

2,2-dimethyl-4-(2-oxo-4-hydroxy-1,2-dihydro-1-pyridyl)-6-nitro-2H-1,3-benzoxazine 2,2-dimethyl-4-(2-hydroxy-4-pyridyl-oxy)-6-nitro-2H-1,3-benzoxazine 2,2-dimethyl-4-(2-oxo-4-hydroxy-1,2-dihydro-1-pyridyl)-6-methoxycarbonyl-2H-1,3-benzoxazine 2,2-dimethyl-4-(2-hydroxy-4-pyridyl-oxy)-6-methoxycarbonyl-2H-1,3-benzoxazine 2,2-dimethyl-4-(3-hydroxy-6-oxo-1,6-dihydro-1-pyridazinyl)-6-bromo-2H-1,3-benzoxazine 2,2-dimethyl-4-(6-hydroxy-3-pyridazinyl-oxy)-6-bromo-2H-1,3-benzoxazine, m.p. 196°–198°

2,2-dimethyl-4-(3-hydroxy-6-oxo-1,6-dihydro-1-pyridazinyl)-6-nitro-2H-1,3-benzoxazine 2,2-dimethyl-4-(6-hydroxy-3-pyridazinyl-oxy)-6-nitro-2H-1,3 -benzoxazine 2,2-dimethyl-4-(3-hydroxy-6-oxo-1,6-dihydro-1-pyridazinyl)-6-methoxycarbonyl-2H-1,3-benzoxazine.

EXAMPLE 2

A mixture of 22 g of IIa, 1.9 g of 1H-2-pyridone, 1 ml of pyridine and 10 ml of ethanol is heated at 100° (in the tube) for 2 hours. The mixture is evaporated and subjected to customary work-up, and "A" and "B" are obtained on chromatographic separation.

EXAMPLE 3

1.2 g of 80% NaH are added to a solution of 2.65 g of 2,2-dimethyl-4-bromo-6-cyano-2H-1,3-benzoxazine (obtainable from 2,2-dimethyl-6-cyano-3,4-dihydro-2H-1,3-benzoxazin-4-one and $SOBr_2$) and 0.95 g of 2H-1-pyridone in 20 ml of DMSO, and the mixture is stirred at 20° for 3 days. Customary work-up gives "A" and "B".

EXAMPLE 4

2,2-Dimethyl-4-(3-hydroxy-2-pyridylamino)-6-cyano-2H-1,3-benzoxazine is obtained analogously to Example 2 from IIa and 2-amino-3-hydroxypyridine.

EXAMPLE 5

2,2-Dimethyl-4-(2-oxo-pyrrolidino)-6-cyano-2H-1,3-benzoxazine is obtained analogously to Example 1 from IIa and pyrrolidin-2-one. m.p. 186°-187°.

The following are obtained analogously:
2,2-dimethyl-4-(2-oxo-pyrrolidino)-6-nitro-2H-1,3-benzoxazine
2,2-dimethyl-4-(2-oxo-piperidino)-6-cyano-2H-1,3-benzoxazine
2,2-dimethyl-4-(2-oxo-piperidino)-6-nitro-2H-1,3-benzoxazine.

EXAMPLE 6

A solution of 1 g of 2,2-dimethyl-4-(2-oxo-1,2-dihydro-1-pyridyl)-6-nitro-2H-1,3-benzoxazine in 24 ml of methanol is hydrogenated to completion at 20° and 1 bar on 0.5 g of 5% Pd/C. The mixture is filtered, the filtrate is evaporated, and customary work-up (with dilute sodium hydroxide solution/dichloromethane) gives 2,2-dimethyl-4-(2-oxo-1,2-dihydro-1-pyridyl)-6-amino-2H-1,3-benzoxazine.

EXAMPLE 7

A solution of 1 g of 2,2-dimethyl-4-(2-oxo-1,2-dihydro-1-pyridyl)-6-amino-2H-1,3-benzoxazine in 15 ml of formic acid and 1 ml of pyridine is boiled for 16 hours and evaporated. Customary work-up gives 2,2-dimethyl-4-(2-oxo-1,2-dihydro-1-pyridyl)-6-formamido-2H-1,3-benzoxazine.

EXAMPLE 8

A mixture of 1 g of 2,2-dimethyl-4-(2-oxo-1,2-dihydro-1-pyridyl)-6-amino-2H-1,3-benzoxazine, 10 ml of acetic anhydride and 10 ml of pyridine is left to stand at 20° for 16 hours. The mixture is evaporated, and the residue is purified by chromatography to give 2,2-dimethyl-4-(2-oxo-1,2-dihydro-1-pyridyl)-6-acetamido-2H-1,3-benzoxazine.

EXAMPLE 9

HCl is passed into a stirred, boiling solution of 1 g of "B" in 50 ml of methanol and 2 ml of water for 14 hours. The mixture is cooled overnight to 0°. The 2,2-dimethyl-4-(2-oxo-1,2-dihydro-1-pyridyl)-2H-1,3-benzoxazine-6-carboxylic acid which precipitates out is filtered off.

EXAMPLE 10

A mixture of 2.79 g of "B", 31 g of $Na_3PO_4.12H_2O$, 28 ml of pyridine, 28 ml of water, 67 ml of acetic acid and 25 g of Raney nickel (moist with water) is stirred at 20° for 3 hours. The mixture is filtered and subjected to customary work-up to give 2,2-dimethyl-4-(2-oxo-1,2-dihydro-1-pyridyl)-6-formyl-2H-1,3-benzoxazine.

EXAMPLE 11

2.79 g of "B" are dissolved in 40 ml of tert.-butanol, and 5.6 g of powdered KOH are added with stirring. The mixture is boiled for one hour and subjected to customary work-up to give 2,2-dimethyl-4-(2-oxo-1,2-dihydro-1-pyridyl)-6-carbamoyl-2H-1,3-benzoxazine.

EXAMPLE 12

$H_2S$ is passed into a solution of 2.79 g of "B" in a mixture of 20 ml of pyridine and 10 ml of triethylamine at 20° for 5 hours, and the mixture is evaporated and subjected to customary work-up to give 2,2-dimethyl-4-(2-oxo-1,2-dihydro-1-pyridyl)-6-thiocarbamoyl-2H-1,3-benzoxazine.

EXAMPLE 13

A mixture of 2.79 g of "B", 8.08 g of Lawesson reagent and 50 ml of toluene is boiled for one hour under $N_2$. Customary work-up gives 2,2-dimethyl-4-(2-thioxo-1,2-dihydro-1-pyridyl)-6-cyano-2H-1,3-benzoxazine.

The following are obtained analogously:
2,2-dimethyl-4-(2-thioxo-1,2-dihydro-1-pyridyl)-6-bromo-2H-1,3-benzoxazine
2,2-dimethyl-4-(2-thioxo-1,2-dihydro-1-pyridyl)-6-nitro-2H-1,3-benzoxazine

EXAMPLE 14

A mixture of 295 mg of 2,2-dimethyl-4-(2-oxo-1,2-dihydro-4-pyridyloxy)-6-cyano-2H-1,3-benzoxazine, 20 ml of acetone, 400 mg of $K_2CO_3$ and 0.2 ml of dimethyl sulfate is boiled for 2 hours. The mixture is filtered and subjected to customary work-up to give 2,2-dimethyl-4-(1-methyl-2-oxo-1,2-dihydro-4-pyridyloxy)-6-cyano-2H-1,3-benzoxazine.

EXAMPLE 15

A mixture of 296 mg of 2,2-dimethyl-4-(6-hydroxy-3-pyridazinyloxy)-6-cyano-2H-1,3-benzoxazine, 1 g of $K_2CO_3$, 0.65 ml of dimethyl sulfate and 16 ml of DMF is boiled for 3 hours and subjected to customary work-up. 2,2-Dimethyl-4-(6-methoxy-3-pyridazinyloxy)-6-cyano-2H-1,3-benzoxazine is obtained.

EXAMPLE 16

Analogously to Example 1, 2,2-dimethyl-4-(2-oxo-1,2-dihydro-pyridyl)-6-methoxy-2H-1,3-benzoxazine, m.p. 104°, is obtained from 2,2-dimethyl-4-chloro-6-methoxy-2H-1,3-benzoxazine and 1H-2-pyridone.

Analogously, 2,2-dimethyl-4-(6-hydroxy-3-pyridazinylthio)-6-cyano-2H-1,3-benzoxazine is obtained from IIa and 3-mercapto-6-hydroxy-pyridazine.

Analogously, 2,2-dimethyl-4-(6-hydroxy-3-pyridazinylthio)-6-bromo-2H-1,3-benzoxazine is obtained from 2,2-dimethyl-4-chloro-6-bromo-2H-1,3-benzoxazine.

EXAMPLE 17

A solution of diazomethane in ether is added dropwise at 20° to a solution of 1 g of 2,2-dimethyl-4-(6-hydroxy-3-pyridazinyl-oxy)-6-cyano-2H-1,3-benzoxazine, until there remains a yellow color. The solution is concentrated, and 2,2-dimethyl-4-(1,6-dihydro-1-methyl-6-oxo-3-pyridazinyl-oxy)-6-cyano-2H-benzoxazine is obtained.

Analogously 2,2-dimethyl-4-(1,6-dihydro-1-methyl-6-oxo-3-pyridazinyl-oxy)-6-bromo-2H-1,3-benzoxazine is obtained from the corresponding 6-bromo compound.

The examples below relate to pharmaceutical preparations containing compounds of the formula I or physiologically acceptable salts thereof:

EXAMPLE A

Tablets

A mixture of 1 kg of "B", 80 kg of lactose, 24 kg of potato starch, 4 kg of talc and 2 kg of magnesium stearate is tabletted in the customary way in a manner such that each tablet contains 1 mg of active compound.

EXAMPLE B

Coated tablets

Tablets are pressed analogously to Example A and are subsequently coated in a customary manner with a coating of saccharine, potato starch, talc, tragacanth and coloring.

EXAMPLE C

Capsules

Hard gelatin capsules are filled in a customary way with 1 kg of 2,2-dimethyl-4-(6-hydroxy-3-pyridazinyloxy)-6-cyano-2H-1,3-benzoxazine in a manner such that each capsule contains 0.5 mg of active compound.

EXAMPLE D

Ampoules

A solution of 50 g of "B" in 70 l of 1,2-propanediol is made up to 100 l with bidistilled water, filtered sterile, transferred into ampoules and sealed under sterile conditions. Each ampoule contains 0.5 mg of active compound.

Tablets, coated tablets, capsules or ampoules containing one or more of the other active compounds of the formula I and/or physiologically acceptable salts thereof are obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A benzoxazine derivative of the formula

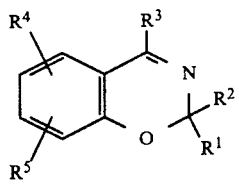

wherein
$R^1$ and $R^2$ are each independently H or A, or, together, are alternatively alkylene having 3-6 C atoms;
$R^3$ is 2-, 3-, or 4-pyridyl-oxy-, 2-, 3-, or 4-pyridyl-thio, oxo-dihydro-pyridyl, or oxodihydro-2-, 3-, or 4-pyridyl-Z-, each of which is unsubstituted or monosubstituted or disubstituted by A, F, Cl, Br, I, OH, OA, OAc, SH, $NO_2$, $NH_2$, AcNH, HOOC and/or AOOC, and those radicals which are not bonded to the benzoxazine ring via Z can also be completely or partially hydrogenated;
$R^4$ and $R^5$ are each H, A, HO, AO, CHO, ACO, ACS, HOOC, AOOC, AO—CS, ACOO, A—C-S—O, hydroxyalkyl having 1-6 C atoms, mercaptoalkyl having 1-6 C atoms, $NO_2$, $NH_2$, NHA, $NA_2$, CN, F, Cl, Br, I, $CF_3$, ASO, $ASO_2$, AO—SO, AO—$SO_2$, AcNH, AO—CO—NH, $H_2NSO$, HANSO, $A_2NSO$, $H_{NSO2}$, $HANSO_2$, $A_2NSO_2$, $H_2NCO$, HANCO, $A_2NCO$, $H_2NCS$, $A_2NCS$, ASONH, $ASO_2NH$, AOSONH, $AOSO_2NH$, ACO-alkyl, nitroalkyl, cyano-alkyl, A—C(=NOH) or A—C(=$NNH_2$);
Z is O, S or NH;
n is 0 or 1;
A is alkyl having 1-6 C atoms;
-alkyl is alkylene having 1-6 atoms; and
Ac is alkanoyl having 1-8 C atoms or aroyl having 7-11 C atoms;
or a physiologically acceptable salt thereof.

2. a) 2,2-Dimethyl-4-(2-oxo-1,2-dihydro-1-pyridy)-2H-1,3-benzoxazine; b) 2,2-Dimethyl-4-(2-oxo-1,2-dihydro-1-pyridyl)-6-cyano-2H-1,3-benzoxazine; c) 2,2-Dimethyl-4-(2-pyridyl-oxy)-6-cyano-2H-1,3-benzoxazine; or d) 2,2-Dimethyl-4-(2-oxo-1,2-dihydro-1-pyridyl)-6-bromo-2H-1,3-benzoxazine, each a compound of claim 1.

3. A compound according to claim 1, wherein $R^1$ and $R^2$ are each A.

4. A compound according to claim 1, wherein $R^1$ and $R^2$ are each $CH_3$.

5. A compound according to claim 1, wherein $R^1$ and $R^2$ together are alkylene having 3-6 C atoms.

6. A compound according to claim 1, wherein $R^3$ is 2-oxo-1,2-dihydro-1-pyridyl or 2-oxo-4-hydroxy-1,2-dihydro-1-pyridyl.

7. A compound according to claim 1, wherein $R^3$ is 2-pyridyloxy or 2-hydroxy-4-pyridyl-oxy.

8. A compound according to claim 1, wherein $R^3$ is 2-oxo-1,2-dihydro-1-pyridyl.

9. A compound according to claim 1, wherein $R^1$ and $R^2$ are each $CH_3$; and $R^3$ is 2-oxo-1,2-dihydro-1 pyridyl or 2-oxo-4-hydroxy-1,2-dihydro-1-pyridyl.

10. A compound according to claim 1, wherein $R^1$ and $R^2$ are each $CH_3$; and $R^3$ is 2-pyridyloxy or 2-hydroxy-4-pyridyloxy.

11. A compound according to claim 1, wherein $R^1$ and $R^2$ are each $CH_3$; and $R^3$ is 2-oxo-1,2-dihydro-1-pyridyl.

12. A compound according to claim 1, wherein $R^4$ is different from H; and $R^5$ is H.

13. A compound according to claim 1, wherein $R^4$ is different from H and is in the 6-position; and $R^5$ is H.

14. A compound according to claim 1, wherein $R^4$ is $NO_2$, CN, CHO, ACO, HOOC, AOOC, ACOO, F, Cl, Br, I, $CF_3$, $H_2NCO$, or $NH_2$; and $R^5$ is H.

15. A compound according to claim 1, wherein $R^4$ is $NO_2$, CN, CHO, ACO, HOOC, AOOC, ACOO, F, Cl, Br, I, $CF_3$, $H_2NCO$, $H_2NCS$ or $NH_2$ and is in the 6-position; and $R^5$ is H.

16. A pharmaceutical composition comprising a compound according to claim 1 and a physiologically acceptable carrier.

17. A pharmaceutical composition according to claim 16, wherein said compound is present in an amount of about 0.01–5 mg.

* * * * *